United States Patent [19]

Press et al.

[11] Patent Number: 4,835,157

[45] Date of Patent: May 30, 1989

[54] THIENO- AND FUROPYRIMIDINE-2,4-DIONE PIPERIDINE DERIVATIVES AS SEROTONIN ANTAGONISTS AND ALPHA ADRENERGIC BLOCKING AGENTS

[75] Inventors: Jeffery B. Press, Rocky Hill; Ronald K. Russell, Titusville, both of N.J.

[73] Assignee: Ortho Pharmaceutical Corporation, Raritan, N.J.

[21] Appl. No.: 168,199

[22] Filed: Mar. 15, 1988

[51] Int. Cl.$^4$ ............... C07D 491/00; A61K 31/505
[52] U.S. Cl. .................................... 514/258; 544/278
[58] Field of Search ...................... 544/278; 514/258

[56] References Cited

U.S. PATENT DOCUMENTS 4,670,560 6/1987 Press et al. ........................ 544/278
4,703,120 10/1987 Press ................................. 544/278
4,707,550 11/1987 Press et al. ........................ 544/278

OTHER PUBLICATIONS

Kaplan, Arch. Intern. Med., vol. 143, 1983, pp. 255–259.
Royal Society of Medicine International Congress and Symposium Series, Rawlins et al., 1981, No. 41.
Buhler et al., Journal of Cardiovascular Pharmacology, vol. 7, Supplement 7, 1985.
Houston et al., Drugs, vol. 31, pp. 149–163, (1986).
Janssen, TIPS Reviews, 4, No. 198, 1983.
Janssen, Journal of Cardiovascular Pharmacology, No. 7, Suppl. 7, pp. 52–511, 1985.

*Primary Examiner*—John M. Ford
*Assistant Examiner*—Robert C. Whittenbaugh
*Attorney, Agent, or Firm*—Benjamin F. Lambert

[57] ABSTRACT

Novel thienopyrimidine-2,4-dione piperidine derivatives and novel furo[3,4-d]pyrimidine-2,4-dione piperidine derivatives are described. The novel piperidine derivatives are selective serotonin antagonists and alpha adrenergic blocking agents with cardiovascular, gastrointestinal and central nervous system activites.

38 Claims, No Drawings

THIENO- AND FUROPYRIMIDINE-2,4-DIONE PIPERIDINE DERIVATIVES AS SEROTONIN ANTAGONISTS AND ALPHA ADRENERGIC BLOCKING AGENTS

BACKGROUND OF THE INVENTION

The present invention relates to novel thienopyrimidine-2,4-dione piperidine derivatives and novel furopyrimidine-2,4-dione piperidine derivatives as described further below. The novel compounds are useful as serotonin antagonists and α-adrenergic blockers with cardiovascular, gastrointestinal and central nervous system activities.

Hypertension afflicts 10–20% of the adult population and is a major cause of many forms of cardiovascular disease (Kaplan, *Arch. Intern. Med.* 143, 255 (1983)). One method to reduce blood pressure of a hypertensive patient is by the administration of a peripheral $\alpha_1$-adrenergic antagonist such as prazosin ("Prazosin: Pharmacology, Hypertension and Congestive Heart Failure," M. D. Rawlins, Ed., 1981). This type of drug effects peripheral vasodilation which reduces the pressure necessary for circulation. Another method to treat hypertension is by the administration of a selective serotonin (5-HT$_2$) antagonist such as ketanserin (Proceedings of the 10th Scientific Meeting of the International Society of Hypertension, *J. Cardiovascular Pharmacol.* 7, Suppl. 7 (1985)). The role of serotonin (5-HT$_2$) in the vascular system has been reviewed in detail (Houston et al., *Drugs* 31, 149 (1986)). Drugs of this type have also been shown to inhibit platelet aggregation, tracheal smooth muscle contraction and gastrointestinal smooth muscle contraction, and to treat CNS disorders such as anxiety (Janssen, *Trends in Pharmacological Sciences* 4, 198 (1983); Janssen, *J. Cardiovascular Pharmacol.* 7, Suppl. 7 (1985)). They are therefore useful as cardioprotective agents, antianginals, afterload reducing agents in congestive heart failure and in the treatment of various peripheral vascular disorders.

Press et al., U.S. Pat. No. 4,670,560, discloses the use of thienopyrimidine-2,4-dione derivatives as antihypertensive or general vasodilating agents. All of the compounds claimed by Press et al. are aryl piperazine derivatives of the general formula

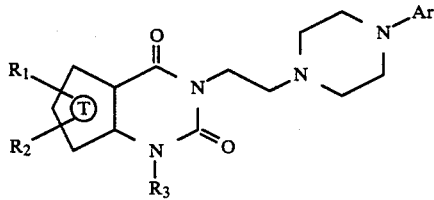

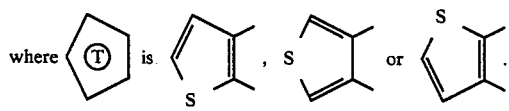

U.S. patent application Ser. No. 856,561, filed on Apr. 28, 1986, which issued as U.S. Pat. No. 4,703,120 on Oct. 27, 1987, claims furo[3,4-d]pyrimidine-2,4-dione derivatives which are useful as antihypertensive or general vasodilating agents. All of the compounds claimed in that application are aryl piperazine derivatives of the general formula

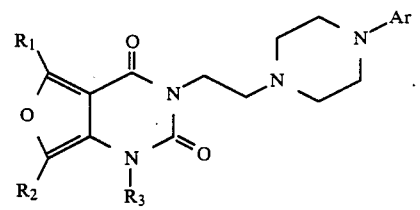

SUMMARY OF THE INVENTION

The present invention is directed to thienopyrimidine-2,4-dione piperidine derivatives and furo[3,4-d]pyrimidine-2,4-dione piperidine derivatives of the formula

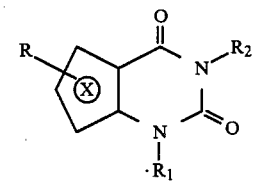

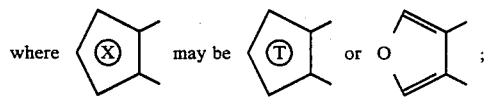

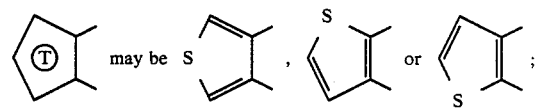

R may be hydrogen, $C_1$–$C_3$ alkyl, Cl, Br or nitro;
R$_1$ may be hydrogen, $C_1$–$C_6$ alkyl, $C_3$–$C_6$ branched-chain alkyl, $C_3$–$C_6$ alkenyl, $C_3$–$C_6$ alkynyl or —COR$_3$;
R$_2$ may be

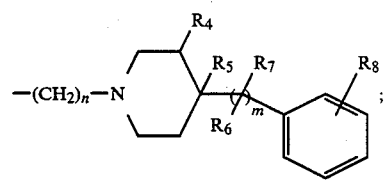

R$_3$ may be $C_1$–$C_6$ alkyl, phenyl or phenyl substituted or polysubstituted with Cl, Br, F, I, $C_1$–$C_3$ alkyl, $C_1$–$C_3$ alkoxy, CF$_3$, acetyl, nitro or acetamido;
R$_4$ may be hydrogen, or R$_4$ together with R$_5$ may be a double bond;
R$_5$ may be hydrogen, or R$_5$ together with R$_4$ may be a double bond, or R$_5$ together with R$_6$ may be a double bond;
R$_6$ together with R$_5$ may be a double bond, or R$_6$ together with R$_7$ may be a carbonyl oxygen;
R$_7$ may be phenyl or phenyl substituted with Cl, Br, F, I, $C_1$–$C_3$ alkyl, $C_1$–$C_3$ alkoxy or CF$_3$, or R$_7$ together with R$_6$ may be a carbonyl;
R$_8$ may be hydrogen, Cl, Br, F, CF$_3$, $C_1$–$C_6$ alkyl or $C_1$–$C_3$ aklkoxy;
m is 0 or 1; and n may be 2-6;
with the provisos that
when

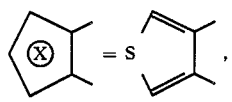

then R is not $C_1$–$C_3$ alkyl;
when

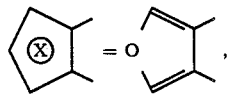

R is hydrogen;
when $R_4$ and $R_5$ are hydrogen, $R_6$ together with $R_7$ is a carbonyl oxygen and m is 1,
when $R_4$ together with $R_5$ is a double bond, m is 0, and
when $R_4$ is hydrogen and $R_5$ together with $R_6$ is a double bond, $R_7$ is phenyl or phenyl substituted with Cl, Br, F, I, $CF_3$, $C_1$–$C_3$ alkyl or $C_1$–$C_3$ alkoxy, and m is 1;

The compounds of formula I are useful as selective serotonin antagonists and α-adrenergic blocking agents with cardiovascular, gastrointestinal and central nervous system activities.

DETAILED DESCRIPTION OF THE INVENTION

The invention in its broadest aspects relates to thienopyrimidine-2,4-dione piperidine compounds and furo[3,4-d]pyrimidine-2,4-dione piperidine compounds which have selective serotonin antagonist activity and cardiovascular activity in mammals. The thienopyrimidine-2,4-dione piperidine compounds and the furo[3,4-d]pyrimidine-2,4-dione piperidine compounds of the invention demonstrating selective serotonin antagonist activity, cardiovascular, CNS and gastrointestinal activities are shown in formula I above.

The thienopyrimidine component of formula I may be either thieno[3,4-d]pyrimidine, thieno[2,3-d]pyrimidine or thieno[3,2-d]pyrimidine.

The preferred compounds of the present invention are those in which $R_8$ is fluorine and (1) $R_4$ and $R_5$ are hydrogen and $R_6$ together with $R_7$ is a carbonyl oxygen, or (2) $R_4$ hydrogen, $R_5$ together with $R_6$ is a double bond and $R_7$ is fluoro-substituted phenyl.

The thieno compounds of formula I can be prepared according to Scheme I. The furo compounds of formula I can be prepared according to Scheme II.

SCHEME I

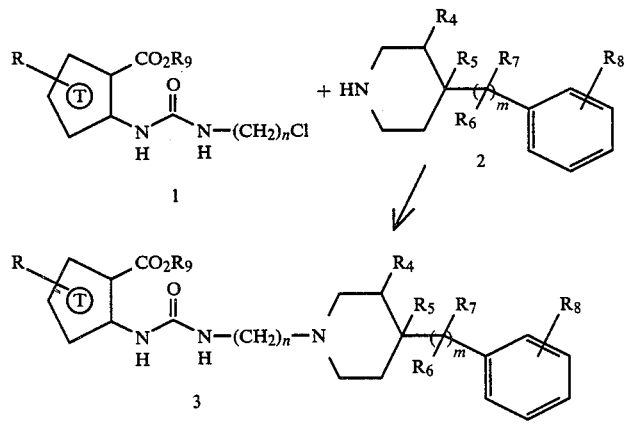

A crystalline chloroalkyl urea 1 wherein $R_9$ is $C_1$–$C_2$ alkyl (U.S. Pat. No. 4,670,560) is reacted with a substituted piperidine 2 in an inert solvent and heated to reflux for about 18–96 hours in the presence of a base to produce the alkylpiperidine 3. Suitable inert solvents for this step include tetrahydrofuran (THF), dioxane, dimethylformamide (DMF), acetonitrile and isopropanol. A preferred base for use in this step is sodium bicarbonate with sodium iodide as a catalyst.

The alkylpiperidine 3 may then be converted to a thienopyrimidine-2,4-dione piperidine 4. The conversion is accomplished in an alcoholic solvent which contains an alkali metal base at about 25° C. to about 65° C. for about one-half hour to about four days. Suitable alcohols include methanol, ethanol and isopropanol. Preferred alkali metal bases include sodium hydroxide, potassium hydroxide, sodium hydride and sodium carbonate.

The thienopyrimidine-2,4-dione 4 may be converted to a 1-substituted thienopyrimidine-2,4-dione piperidine 5. The thienopyrimidine-2,4-dione 4 is reacted with a halide of the formula $R_1X$, where $R_1$ may be any of the substituents described above except hydrogen, in the presence of a base such as sodium hydride in an inert solvent such as dimethylformamide (DMF) or tetrahydrofuran (THF), at about 25° C. for about one-half hour to about 48 hours. The thienopyrimidine-2,4-dione 4 may also be reacted with a carboxylic acid chloride such as acetyl chloride or benzoyl chloride in methylene chloride in the presence of triethylamine to give 1-acyl-substituted 4.

SCHEME II

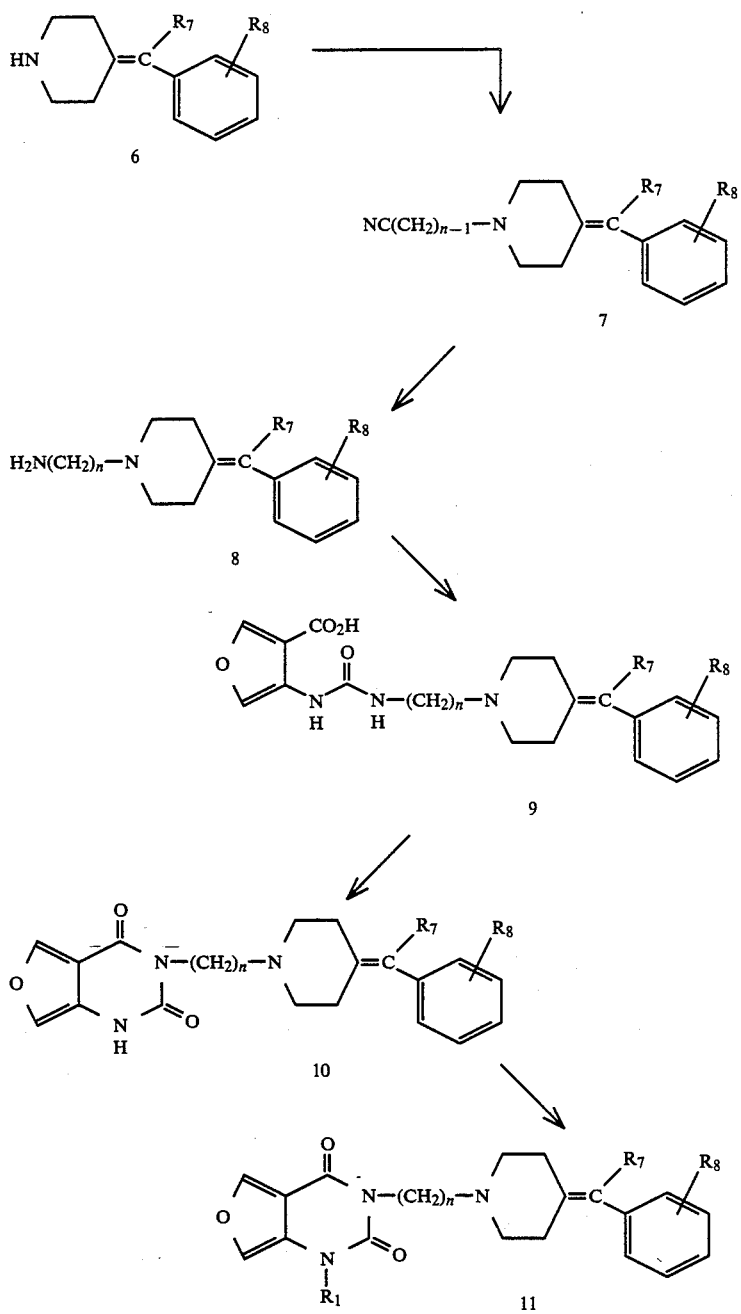

A piperidylidene 6 is reacted with a chloroalkylnitrile of the formula Cl(CH$_2$)$_n$CN in the presence of a base, such as sodium bicarbonate, in an inert solvent such as benzene and heated to reflux for about 16 to about 48 hours to produce the cyanoalkylpiperidylidene 7. The cyanoalkylpiperidylidene 7 is added to a suspension of lithium aluminum hydride in diethyl ether and heated to reflux for about 12–24 hours to produce a piperidinylalkylamine 8. The piperidinylalkylamine 8 is reacted with 4H-furo[3,4-d][1,3]oxazine-2(1H),4-dione (J. B. Press et al., *J. Org. Chem.* 46, 3853 (1981) in an inert solvent at about 25° C. for about 16 to about 24 hours to yield a carboxyfuranpiperidylidene 9. Suitable inert solvents include THF, dioxane, DMF and acetonitrile. The carboxyfuranpiperidylidene 9 is converted to furo[3,4-d]pyrimidine-2,4-dione piperidine 10 by heating to reflux for about four hours to about 12 hours in the presence of a dehydrating agent such as N,N'-carbonyldiimidazole in an inert solvent such as THF. A 1-substituted derivative 11 is prepared by reacting the piperidine 10 with a halide of the formula R$_1$X, where R$_1$ may be any substituent described above except hydrogen, in the presence of a base in an inert solvent.

Pharmaceutical compositions containing a compound of the present invention as the active ingredient in intimate admixture with a pharmaceutical carrier can be prepared according to conventional pharmaceutical compounding techniques. The carrier may take a wide variety of forms depending on the form of preparation desired for administration, e.g., intravenous, oral or parenteral. In preparing the compositions in oral dosage form, any of the usual pharmaceutical media may be employed, such as, for example, water, glycols, oils, alcohols, flavoring agents, preservatives, coloring agents and the like in the case of oral liquid preparations (such as, for example, suspensions, elixirs and solutions); or carriers such as starches, sugars diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. For parenterals, the carrier will usually comprise sterile water, though other ingredients, for example, to aid solubility or for preservative purposes, may be included. Injectable suspensions may also be prepared, in which case appropriate liquid carriers, suspending agents and the like may be employed. The pharmaceutical compositions will generally contain dosage unit, e.g., tablet, capsule, powder, injection, teaspoonful and the like, from about 1 to about 100 mg/kg, and preferably from about 5 to about 25 mg/kg of the active ingredient.

The following examples describe the invention in greater particularity and are intended to be a way of illustrating but not limiting the invention.

EXAMPLE 1

3-[2-[4-(4-Fluorobenzoyl)piperidin-1-yl]ethyl]-thieno[3,2-d]pyrimidine-2,4-dione A mixture of N-(2-carbomethoxythien-3-yl)-N-(2-chloroethyl)urea (U.S. Pat. No. 4,670,560) (4.0 g, 15.2 mmol), 4-(4-fluorobenzoyl)piperidine hydrochloride (9.24 g, 38.0 mmol), sodium bicarbonate (4.47 g, 53.2 mmol) and sodium iodide (0.50 g, 3.3 mmol) in tetrahydrofuran (100 ml) was heated to reflux for four days. The solvent was evaporated in vacuo, and the resultant residue was treated with water (100 ml). The product was extracted into methylene chloride (2×75 ml) and dried over magnesium sulfate. The product was purified by flash chromatography on silica gel 60 (250 g) using 2% methanol in methylene chloride as the eluant to give N-(2-carbomethoxythien-3-yl)-N-[2-[2-[4-(4-fluorobenzoyl)piperidin-1-yl]ethyl]urea (4.07 g, 62% yield) as a colorless solid. IR(KBr): 1540, 1560, 1585, 1660, 2770, 2920, 3300 and 3360 cm$^{-1}$; MS (DCI), m/z 434 (MH+); $^1$H NMR (CDCl$_3$): δ 1.6–2.4 (m, 6H), 2.53 (m, 2H), 2.8–3.6 (m, 5H), 5.5 (br s, 1H), 7.1 (t, J=8 Hz, 2H), 7.26 (d, J=5 Hz, 1H), 7.80–8.07 (m, 3H) and 9.45 (br s, 1H).

For C$_{21}$H$_{24}$FN$_3$O$_4$S: Theor.: C, 58.18; H, 5.58; N, 9.69; F, 4.38; S, 7.39. Found: C, 58.37; H, 5.77; N, 9.61; F, 4.30; S, 7.40.

A solution of the above urea (1.2 g, 2.8 mmol) and 50% sodium hydroxide (0.213 g, 2.7 mmol) in methanol (30 ml) was stirred at room temperature for 24 hours. The solution was acidified with acetic acid (0.5 ml) and the solvent was evaporated in vacuo. The residue was treated with water (75 ml) and neutralized with sodium bicarbonate. The resultant solid was collected by filtration, washed with water, air-dried and triturated in hot acetone to give the named compound (1.04 g, 94% yield) as a colorless solid, mp 141°–143° C. IR(KBr): 1580, 1640, 1695, 2790, 2940, 3200 and 3240 cm$^{-1}$; MS (DCI), 402 m/z (MH+); $^1$H NMR (DMSO-d$_6$): δ 1.47–1.60 (m, 2H), 1.70–1.78 (m, 2H), 2.11–2.17 (m, 2H), 2.93–3.05 (m, 2H), 3.34–3.42 (m, 2H), 4.00 (t, J=7 Hz, 2H), 6.91 (d, J=5 Hz, 1H), 7.34 (s, J=8 Hz, 2H) and 8.03–8.11 (m, 3H).

Theor. C$_{20}$H$_{20}$FN$_3$O$_3$S: C, 59.83; H, 5.02; N, 10.47. Found: C, 59.38; H, 5.28; N, 10.22.

EXAMPLE 2

3-[2-[4-(4-Fluorobenzoyl)piperidin-1-yl]ethyl]-thieno[2,3-d]pyrimidine-2,4-dione A mixture of N-(3-carboethoxythien-2-yl)-N-(2-chloroethyl)urea (U.S. Pat. No. 4,670,560) (5.60 g, 20.2 mmol), 4-(4-fluorobenzoyl)piperidine hydrochloride (12.27 g, 50.5 mmol), sodium bicarbonate (5.94 g, 70.7 mmol) and sodium iodide (0.50 g, 3.3 mmol) in tetrahydrofuran (200 ml) was heated at reflux for four days. The solvent was evaporated in vacuo, and the resultant residue was treated with water (100 ml). The product was extracted into methylene chloride (2×100 ml) and dried over magnesium sulfate. The product was purified by flash chromatography on silica gel 60 (250 g) using 2.5% methanol in methylene chloride as the eluant to give N-(3-carboethoxythien-2-yl)-N-[2-[4-(4-fluorobenzoylpiperidin-1-yl]ethyl]urea (6.33 g, 70% yield) as a pale yellow solid, mp 58°–62° C. IR(KBr): 1543, 1598, 1674 and 1677 cm$^{-1}$; MS (DCI), m/z 448 (MH+); $^1$H NMR (DMSO-d$_6$); δ 1.30 (t, J=7 Hz, 3H), 1.50–2.60 (m, 7H), 3.67–3.40 (m, 6H), 4.30 (q, J=7 Hz, 2H), 6.75 (d, J=6 Hz, 1H), 7.05 (d, J=6 Hz, 1H), 7.32 (t, J=8 Hz, 2H), 7.75–8.15 (m, 3H) and 10.12 (br s, 1H).

For C$_{22}$H$_{26}$FN$_3$O$_4$S: Theor.: C, 59.04; H, 5.86; N, 9.39; F, 4.25; S, 7.16. Found: C, 58.58; H, 6.09; N, 9.24; F, 4.26; S, 7.19.

A solution of the above urea (6.19 g, 13.8 mmol) and 50% sodium hydroxide (0.553 g, 13.8 mmol) in methanol (100 ml) was stirred at room temperature for four days. The solution was acidified with acetic acid (2.0 ml) and the solvent was evaporated in vacuo. The residue was treated with water (100 ml) and neutralized with sodium bicarbonate. The resultant solid was collected by filtration, washed with water, air-dried and triturated in hot ethanol to give the title compound (4.32 g, 78% yield) as a colorless solid, mp 231°–235° C. IR(KBr): 1596, 1665, 1677 and 1704 cm$^{-1}$; MS (DCI), m/z 402 (MH+); $^1$H NMR (DMSO-d$_6$): δ 1.35–3.55 (m, 12H), 3.95 (t, J=7 Hz, 2H), 7.05 (d, J=6 Hz, 1H), 7.13 (d, J=6 Hz, 1H), 7.30 (t, J=8 Hz, 2H), and 8.00 d of d, J=7 Hz, J=8 Hz, 2H).

For C$_{20}$H$_{20}$FN$_3$O$_3$S: Theor.: C, 59.83; H, 5.02; N, 10.47; F, 4.73; S, 7.99. Found: C, 59.58; H, 5.18; N, 10.26; F, 4.53; S, 7.92.

EXAMPLE 3

1-Acetyl-3-[2-[4-(4-fluorobenzoyl)piperidin-1-yl]ethyl]-thieno[2,3-d]pyrimidine-2,4-dione A mixture of 3-[2-[4-(4-fluorobenzoyl)piperidin-1-yl]ethyl]thieno[2,3-d]pyrimidine-2,4-dione of Example 2 (1.7 g, 4.2 mmol), acetyl chloride (0.33 ml, 4.6 mmol) and triethylamine (1.8 ml, 12.6 mmol) in methylene chloride (40 ml) was stirred at room temperature for two days. The resultant solution was washed with H$_2$O (2×50 ml), and then dried over magnesium sulfate. The solvent was evaporated in vacuo, and the resultant residue was purified by flash chromatography on silica gel 60 (80 g) using 2% methanol in methylene chloride as the eluant to give the named compound (1.3 g, 69% yield) as a colorless solid, mp 137°-141° C. IR(KBr): 1630, 1700 and 1775 cm$^{-1}$; MS (DCI), m/z 444 (MH$^+$); $^1$H NMR (CDCl$_3$): δ 1.76-1.85 (m, 4H), 2.19-2.25 (m, 2H), 2.70 (t, J=7 Hz, 2H), 2.86 (s, 3H), 3.12-3.25 (m, 3H), 4.22 (t, J=7 Hz, 2H), 7.07 (d, J=6 Hz, 1H), 7.13 (t, J=8 Hz, 2H), 7.40 (d, J=6 Hz, 1H), 7.94-7.97 (m, 2H).

For C$_{22}$H$_{22}$FN$_3$O$_4$S: Theor.: C, 59.58; H, 5.00; N, 9.47; F, 4.28; S, 7.23. Found: C, 59.73; H, 5.18; N, 9.42; F, 4.25; S, 7.54.

EXAMPLE 4

3-[2-[4-[Bis(4-fluorophenyl)methylene]piperidin-1-yl]ethyl]thieno[3,4-d]pyrimidine-2,4-dione A mixture of N-(3-carbomethoxythien-4-yl)-N-(2-chloroethyl)urea (U.S. Pat. No. 4,670,560) (2.56 g, 9.74 mmol), bis(4-fluorophenyl)methyl-4-piperilydene (U.S. Pat. No. 4,485,107) (4.17 g, 14.62 mmol) sodium bicarbonate (3.27 g, 39.0 mmol) and sodium iodide (0.73 g, 4.87 mmol) in isopropanol (20 ml) was heated to reflux for 24 hours. The solvent was evaporated in vacuo and the residue was treated with water (50 ml). The resultant solid was collected by filtration, washed with water, air-dried and purified by flash chromatography on silica gel 60 (250 g) using 3% methanol in methylene chloride as the eluant to give the title compound (2.17 g, 46% yield), mp 204°-206° C. IR(KBr): 1675 and 1700 cm$^{-1}$; MS(DCI), m/z 480 (MH$^+$); $^1$H NMR (DMSO-d$_6$): δ 2.47-2.50 (m, 4H), 2.76-2.79 (m, 4H), 2.84 (t, J=6 Hz, 2H), 4.28 (t, J=6 Hz, 2H), 6.61 (d, J=3 Hz, 1H), 7.02-7.35 (m, 4H) and 8.14 (d, J=3 Hz, 1H).

For C$_{26}$H$_{23}$F$_2$N$_3$O$_2$S: Theor.: C, 65.12; H, 4.83; N, 8.76; F, 7.92; S, 6.69. Found: C, 65.34; H, 4.89; N, 8.81; F, 7.77; S, 6.92.

EXAMPLE 5

3-[2-[4-[Bis(4-fluorophenyl)methylene]piperidin-1-yl]ethyl]thieno[3,2-d]pyrimidine-2,4-dione A mixture of N-(2-carbomethoxythien-3-yl)-N-(2-chloroethyl)urea (U.S. Pat. No. 4,670,560) (2.0 g, 7.61 mmol), bis(4-fluorophenyl)methyl-4-piperilydene (3.2 g, 11.4 mmol), sodium bicarbonate (2.55 g, 30.4 mmol) and sodium iodide (0.57 g, 3.81 mmol) in isopropanol (15 ml) was heated to reflux for 16 hours. The solvent was evaporated in vacuo and the residue was treated with water (50 ml). The resultant solid was collected by filtration, washed with water and air dried. The product was purified by flash chromatography on silica gel 60 (250 g) using 4% methanol in methylene chloride as the eluant. The title compound was further purified by recrystallization from ethanol to give a colorless solid (0.80 g, 22% yield), mp 207°-208° C. IR(KBr): 1630 and 1710 cm$^{-1}$; MS (DCI), m/z 480 (MH$^+$): $^1$H NMR (DMSO-d$_6$): δ 2.20-2.23 (m, 4H), 2.51-2.54 (m, 6H), 3.99 (t, 2H), 6.92 (d, J=6 Hz, 1H), 7.12-7.16 (m, 8H) and 8.05 (d, J=6 Hz, 1H).

For C$_{26}$H$_{23}$F$_2$N$_3$O$_2$S: Theor.: C, 65.12; H, 4.83; N, 8.76; F, 7.92; S, 6.69. Found: C, 65.12; H, 5.02; N, 8.71; F, 8.06; S, 7.02.

EXAMPLE 6

3-[2-[4-[Bis(4-fluorophenyl)methylene]piperidin-1-yl]ethyl]thieno[2,3-d]pyrimidine-2,4-dione A mixture of N-(3-carboethoxythien-2-yl)-N-(2-chloroethyl)urea (U.S. Pat. No. 4,670,560) (2.10 g, 7.6 mmol), bis-(4-fluorophenyl)methyl-4-piperilydene (3.2 g, 11.4 mmol), sodium bicarbonate (2.55 g, 30.4 mmol) and sodium iodide (0.57 g, 3.81 mmol) in isopropanol (15 ml) was heated to reflux for 16 hours. The solvent was evaporated in vacuo and the residue was treated with water (50 ml). The resultant solid was collected by filtration, washed with water and air-dried. The product was purified by flash chromatography on silica gel 60 (250 g) using 4% methanol in methylene chloride to give the title compound (0.937 g, 26% yield) as a colorless solid, mp 205°-207° C. IR(KBr): 1510, 1650 and 1715 cm$^{-1}$; MS (DCI), m/z 480 (MH$^+$); $^1$H NMR (DMSO-d$_6$): δ 2.21 (br s, 4H), 2.51 (br s, 6H), 3.97 (t, J=6 Hz, 2H) and 7.06-7.20 (m, 10H).

For C$_{26}$H$_{23}$F$_2$N$_3$O$_2$S: Theor.: C, 65.12; H, 4.83; N, 8.76; F, 7.92; S, 6.69. Found: C, 65.17; H, 4.95; N, 8.58; F, 7.89; S, 6.98.

EXAMPLE 7

3-[2-[4-[Bis(4-fluorophenyl)methylene]piperidin-1-yl]ethyl]-1-(2,2-dimethyl-1-oxopropyl)thieno[3,4-d]pyrimidine-2,4-dione A mixture of 3-[2-[4-[bis(4-fluorophenyl)methylene]piperidin-1-yl]ethyl]thieno[3,4-d]pyrimidine-2,4-dione of Example 4 (0.80 g, 1.7 mmol), trimethylacetyl chloride (0.25 ml, 2.0 mmol) and triethylamine (0.84 ml, 6.0 mmol) in methylene chloride (20 ml) was stirred at room temperature for 16 hours. The reaction mixture was washed with water (2×30 ml) and dried over magnesium sulfate. The solvent was evaporated in vacuo and the residue was purified by flash chromatography on silica gel 60 (80 g) using 1% methanol in methylene chloride as the eluant, to give the title compound (0.35 g, 37% yield) as a colorless solid, mp 69°-72° C. IR(KBr): 1595, 1660 and 1715 cm$^{-1}$; MS (DCI), m/z 564 (MH$^+$); $^1$H NMR (CDCl$_3$): δ 1.44 (s, 9H), 2.34 (t, J=5 Hz, 4H), 2.61 (t, J=5 Hz, 4H), 2.67 (t, J=7 Hz, 2H), 4.17 (t, J=7 Hz, 2H), 6.58 (d, J=3 Hz, 1H), 6.96-7.08 (m, 8H) and 8.25 (d, J=3 Hz, 1H).

For C$_{31}$H$_{31}$F$_2$N$_3$O$_3$S: Theor.: C, 66.06; H, 5.54; N, 7.49; F, 6.74; S, 5.69. Found: C, 65.80; H, 6.04; N, 7.22; F, 6.50; S, 5.93.

EXAMPLE 8

1-Benzoyl-3-[2-[4-[bis(4-fluorophenyl)methylene]piperidin-1-yl]ethylthieno[3,4-d]pyrimidine-2,4-dione A mixture of 3-[2-[4-[bis(4-fluorophenyl)methylene]piperidin-1-yl]ethyl]thieno[3,4-]pyrimidine-2,4-dione of Example 4 (0.738 g, 1.53 mmol), benzoyl chloride (0.23 ml, 2.0 mmol) and triethylamine (0.83 ml, 6.0 mmol) in methylene chloride (30 ml) was stirred at room temperature for 16 hours. The resultant solution was washed with water (2×30 ml) and dried over magnesium sulfate. The solvent was evaporated in vacuo, and the residue purified by flash chromatography on silica gel 60 (80 g) using 2% methanol in methylene chloride as the eluant to give the title compound (0.625 g, 70% yield) as a colorless solid, mp 148°-151° C. IR(KBr): 1590, 1655 and 1715 cm$^{-1}$; MS (DCI), m/z 584 (MH$^+$); $^1$H NMR (CDCl$_3$): δ 2.15-2.75 (m, 10H), 4.15 (t, J=7 Hz, 2H) 6.90-7.90 (m, 14H) and 8.27 (d, J=3 Hz, 1H).

For C$_{33}$H$_{27}$F$_2$N$_3$O$_3$S: Theor.: C, 67.91; H, 4.66; N, 7.20; F, 6.51; S, 5.49. Found: C, 67.85; H, 4.77; N, 7.24; F, 6.29; S, 5.77.

EXAMPLE 9

3-[2-[4-[Bis(4-fluorophenyl)methylene]piperidin-1-yl]ethyl]furo[3,4-d]pyrimidine-2,4-dione A mixture of 4-[bis(4-fluorophenyl)methyl]piperidylidene (U.S. Pat. No. 4,485,107) (5.9 g, 20.7 mmol), chloroacetonitrile (1.45 ml, 22.7 mmol) and sodium bicarbonate (5.21 g, 62.0 mmol) in benzene (150 ml) was heated to reflux in a Dean-Stark apparatus to azeotropically remove water for 16 hours. Chloroacetonitrile (0.5 ml, 7.9 mmol) was added to the mixture, and the mixture was heated for an additional eight hours. The inorganics were removed by filtration and the organic phase was washed with water (75 ml) and saturated aqueous sodium chloride (75 ml) and dried over magnesium sulfate. The solvent was evaporated in vacuo. The resultant residue was taken up in methylene chloride and passed through a pad of silica gel 60. The solvent was evaporated in vacuo and the resultant residue crystallized from hexanes to give 1-cyanomethyl-4-[bis(4-fluorophenyl)methyl]piperidylidene (5.08 g, 76% yield) as a colorless solid, mp 156°–168° C. IR(KBr): 1510 and 1630 cm$^{-1}$; MS (DCI), m/z 324 (MH+); $^1$H NMR (CDCl$_3$): δ 2.25–2.48 (m, 4H), 2.55–2.70 (m, 4H), 3.52 (s, 2H) and 6.80–7.08 (m, 8H).

Theor. C$_{20}$H$_{18}$F$_2$N$_2$: C, 74.06; H, 5.59; N, 8.64; F, 11.71. Found: C, 73.71; H, 5.63; N, 8.58; F, 11.43.

The above piperidylidene (4.86 g, 15.0 mmol) was added in portions to a suspension of lithium aluminum hydride (0.682 g, 18.0 mmol) in diethyl ether (100 ml). The reaction mixture was heated to reflux for four hours. Water (1 ml) was carefully added to the mixture, followed by 15% sodium hydroxide (1 ml) and water (3 ml). The inorganics were removed by filtration, and the organic phase was dried over magnesium sulfate. The solvent was evaporated in vacuo to give 2-[4-[bis(4-fluorophenyl)methylene]piperidin-1-yl]ethylamine (4.9 g, quantitative) as a yellow oil. MS (DCI), m/z 329 (MH+); $^1$H NMR (CDCl$_3$): δ 1.74–1.96 (m, 2H), 2.27–2.58 (m, 8H), 2.82 (t, J=7 Hz, 2H), 3.73 (t, J=7 Hz, 2H) and 6.84–7.15 (m, 8H).

4H-Furo[3,4-d][1,3]oxazine-2(1H),4-dione (Press et al., J. Org. Chem. 46, 3853 (1981)) (2.17 g, 14.2 mmol) was added to a solution of the above ethylamine (4.9 g, 14.9 mmol) in tetrahydrofuran (50 ml), and the mixture was stirred at room temperature for 16 hours. The resultant solid was collected by filtration, washed with diethylether and air dried to give 1-[(3-carboxyfuran-4-yl)ureidoethyl-4-bis(4-fluorophenyl)methyl-4-piperidylidene (4.47 g, 65% yield) as a colorless solid, mp 212°–215° C. (dec). IR(KBr): 1510, 1525, 1595, 1625 and 1680 cm$^{-1}$; $^1$H (NMR (DMSO-d$_6$): δ 2.27–2.58 (m, 6H), 2.78–3.13 (m, 4H), 3.30–3.56 (br s, 2H), 7.03–7.25 (m, 8H), 7.8 (s, 1H) and 7.85 (s, 1H).

For C$_{26}$H$_{25}$F$_2$N$_3$O$_4$: Theor.: C, 64.86; H, 5.23; N, 8.73; F, 7.89. Found: C, 65.15; H, 5.09; N, 8.57; F, 7.55.

A mixture of 1-[(3-carboxyfuran-4-yl)ureidoethyl]-4-bis(4-fluorophenyl)methyl-4-piperidylidene (4.0 g, 8.3 mmol) and N,N'-carbonyldiimidazole (1.68 g, 10.3 mmol) in dry tetrahydrofuran (200 ml) was heated to reflux for four hours. The solvent was evaporated in vacuo and the residue was treated with water (100 ml). The resultant solid was collected by filtration, washed with water, and air dried. The product was purified by flash chromatography on silica gel 60 (350 g) using 3% methanol in methylene chloride as the eluant, to give the title compound (1.35 g, 35% yield) as a colorless solid, mp 185°–186° C. (dec). IR(KBr): 1600, 1670, 1715 and 1745 cm$^{-1}$; MS(DCI), m/z 464 (MH+); $^1$H NMR (DMSO-d$_6$): δ 2.03–2.30 (m, 4H), 2.35–2.62 (m, 6H), 3.90 (t, J=7 Hz, 2H), 6.97–7.18 (m, 8H), 7.56 (d, J=2 Hz, 1H) and 8.40 (d, J=2 Hz, 1H).

For C$_{26}$H$_{23}$F$_2$N$_3$O$_3$: Theor.: C, 67.38H, 5.00; N, 9.07; F, 8.20. Found: C, 67.16; H, 5.06; N, 8.81; F, 8.04.

EXAMPLE 10

3-[2-[4-(4-Fluorobenzoyl)piperidin-1-yl]ethyl]-thieno[3,4-d]pyrimidine-2,4-dione N-(3-Carbomethoxythien-4-yl)-N'-(chloroethyl)urea (U.S. Pat. No. 4,670,560) (5.24 g, 20 mmol) was dissolved in isopropanol (100 ml) and treated successively with 4-(4-fluorobenzoyl)piperidine hydrochloride (9.71 g, 40 mmol), sodium bicarbonate (3.7 g, 44 mmol) and sodium iodide (1.90 g, 12 mmol) and the mixture was heated to reflux under a nitrogen atmosphere for 12 hours. The reaction mixture was reduced to half volume, diluted with water, and concentrated to remove the remainder of the alcohol solvent. The residue was extracted with methylene chloride and the combined organic extracts were dried with saturated brine and magnesium sulfate. After concentration of the extracts, the residue was purified on silica gel using methylene chloride/ethanol/ammonium hydroxide (96:3.5:0.5) as eluant. The title compound was recrystallized from ethanol to give 0.598 g (7.4% yield) of beige crystals, mp 208°–215° C. (dec). IR(KBr): 1707, 1672, 1159, 1033, 974, 860, 835, 766, 671 and 460 cm$^{-1}$; MS (DCI), 402 m/z (MH+); $^1$H NMR (DMSO-d$_6$): δ 1.5–1.7 (m, 4H), 2.1 (br t, J=7 Hz, 2H), 2.9 (br d, 2H), 3.2–3.55 (m, 3H), 3.9 (t, J=6.2 Hz, 2H), 6.8 (d, J=4 Hz, 1H), 7.3 (t, J=9 Hz, 2H), 8.0 (dd, H=5.8 Hz, 2H), 8.2 (d, J=4 Hz, 1H) and 11.5 (br s, 1H).

Theor. C$_{20}$H$_{20}$ FN$_3$O$_3$S: C, 59.83; H, 5.02; N, 10.47. Found: C, 59.57; H, 5.24; N, 10.47.

EXAMPLE 11

1-Acetyl-3-[2-[4-(4-fluorobenzoyl)piperidin-1-yl]ethyl]-thieno[3,4-d]pyrimidine-2,4-dione The title compound was prepared by suspending the 3-[2-[4-(4-fluorobenzoyl)piperidin-1-yl]ethyl]thieno[3,4-d]pyrimidine-2,4-dione (2.0 g, 5 mmol) of Example 10 in CH$_2$Cl$_2$ and treating it with acetyl chloride (469 mg, 6 mmol) and triethylamine (1 equivalent). After stirring at room temperature for 24 hours, the organic phase was washed with water and brine and dried over MgSO$_4$. Solvent removal produced a crude product which was purified by flash silica gel chromatography using EtOAc/hexane (1/1). The title compound was crystallized from CH$_2$Cl$_2$/hexane to give a white solid (337 mg, 15% yield), mp 150°–151° C.

Theor. C$_{22}$H$_{22}$FN$_3$O$_4$S: C, 59.58; H, 5.00; N. 9.47. Found: C, 59.52; H, 5.02; N, 9.57.

EXAMPLE 12

1-Benzoyl-3-[2-[4-(4-fluorobenzoyl)piperidin-1-yl]ethyl]thieno[3,4-d]pyrimidine-2,4-dione The title compound was prepared by the procedure of Example 11 using 2.0 g (5 mmol) of 3-[2-[4-(4-fluorobenzoyl)piperidin-1-yl]ethyl]thieno[3,4-d]pyrimidine-2,4-dione and benzoyl chloride (840 mg, 6 mmol). The named compound (481 mg, 19% yield) was obtained after recrystallization from CH$_2$Cl$_2$/hexane, mp 153.5°–155° C.

13

Theor. $C_{27}H_{24}FN_3O_4S$: C, 64.14; H, 4.78; N, 8.31. Found: C, 64.07; H, 4.77; N, 8.28.

EXAMPLE 13

3-[2-[4-(4-Fluorobenzoyl)piperidin-1-yl]ethyl]-1-(2,2-dimethyl-1-oxopropylthieno[3,4-d]pyrimidine-2,4-dione The title compound was prepared by the procedure of Example 11 using 1.8 g (4.5 mmol) of 3-[2-[4-(4-fluorobenzoyl)piperidin-1-yl]ethyl]thieno[3,4-d]pyrimidine-2,4-dione and pivaloyl chloride (648 mg, 5.4 mmol). There was obtained 920 mg (42% yield) of the title compound after recrystallization from $CH_2Cl_2$/hexane, mp 110°–111° C.

Theor. $C_{25}H_{28}FN_3O_4S$: C, 61.84; H, 5.81; N, 8.65. Found: C, 61.81; H, 5.89; N, 8.53.

EXAMPLE 14

3-[2-[4-(4-Fluorobenzoyl)piperidin-1-yl]ethyl]-1-methylthieno[3,4-d]pyrimidine-2,4-dione The title compound was prepared by dissolving the 3-[2-[4-(4-fluorobenzoyl)piperidin-1-yl]ethyl]thieno[3,4-d]pyrimidine-2,4-dione from Example 10 (1.8 g, 4.6 mmol) in 10 ml of dimethylformamide at 0° C. After treating this solution with NaH (203 mg, 5 mmol) followed by 720 mg (5 mmol) of methyl iodide, the mixture was stirred at room temperature for 24 hours. The reaction was poured into water and extracted with $CH_2Cl_2$. The combined extracts were washed with water and brine and dried over $MgSO_4$. Solvent removal produced a crude product which was purified by flash silica gel chromatography using 2% MeOH/$CH_2Cl_2$. The title compound was crystallized from $CH_2Cl_2$/hexane to give a white solid (1.04 g, 54% yield), mp 176°–178° C.

Theor. $C_{21}H_{22}FN_3O_3S$: C, 60.71; H, 5.34; N, 10.11. Found: C, 60.75; H, 5.41; N, 9.93.

EXAMPLE 15

1-Butyl-3-[2-[4-(4-fluorobenzoyl)piperidin-1-yl]ethyl]-thieno[3,4-d]pyrimidine-2,4-dione 1/4 Hydrate The title compound was produced by the procedure of Example 14 using 2.81 g (7 mmol) of 3-[2-[4-(4-fluorobenzoyl)piperidin-1-yl]ethyl]thieno[3,4-d]pyrimidine-2,4-dione and bromobutane (1.06 g, 7.7 mmol). There was obtained 539 mg (17% yield) of the title compound as a gold-colored solid after recrystallization from $CH_2Cl_2$/hexane, mp 126°–127° C.

Theor. $C_{24}H_{28}FN_3O_3S \cdot \frac{1}{4}H_2O$: C, 62.38; H, 6.21; N, 9.09. Found: C, 62.14; H, 6.21; N, 8.75.

When in the above procedure, pentyl iodide, 1-bromo-2-methylpropane, 4-bromo-1-butene, 6-bromo-1-hexene or propargyl bromide is employed as the alkylating agent, the corresponding 1-pentyl, 1-(2-methylpropyl), 1-buten-4-yl), 1-(hexen-6-yl) or 1-(propyn-3-yl) derivative is obtained.

EXAMPLE 16

3-[2-[4-(4-Fluorobenzoyl)piperidin-1-yl]ethyl]-5-methylthieno[3,4-d]pyrimidine-2,4-dione The title compound was prepared by reacting N-(3-carbomethoxy-4-methylthien-2-yl)-N'-(2-chloroethyl)urea (U.S. Pat. No. 4,670,560) (2.13 g, 7.7 mmol) with 4-(4-fluorobenzoyl)piperidine hydrochloride (2.82 g, 11.6 mmol) in 15 ml of 2-propanol which contained sodium bicarbonate (1.68 g, 20 mmol) and sodium iodide (687 mg, 4.6 mmol) at reflux for 18 hours. After cooling, water was added and the aqueous phase was extracted with chloroform. The organic phase was washed with brine and dried ($MgSO_4$), and the solvent was removed by distillation. The crude product was purified by flash silica gel chromatography using 2% MeOH/$CH_2Cl_2$ and then crystallized from $CH_2Cl_2$/hexane to give 831 mg (26% yield) of the title compound as a white solid, mp 207° C. (discolors), 212°–214° C. (dec).

Theor. $C_{21}H_{22}FN_3O_3S$: C, 60.71; H, 5.34; N, 10.11. Found: C, 60.38; H, ;b 5.35; N, 9.80.

EXAMPLE 17

3-[2-[4-Bis(4-fluorophenyl)methylene]piperidin-1-yl]ethyl]-5-methylthieno[3,4-d]pyrimidine-2,4-dione The title compound was prepared by the procedure of Example 16 using 2.13 g (7.7 mmol) of N-(3-carbomethoxy-2-methylthien-4-yl)-N'-(2-chloroethyl)urea and 2.85 g (7.7 mmol) of 4-[bis(4-fluorophenyl)methylene]piperidine. There was obtained 1.34 g (35% yield) of the title compound as a white solid after recrystallization from $CH_2Cl_2$/hexane, mp 137°–139° C.

Theor. $C_{27}H_{25}F_2N_3O_2S$: C, 65.70; H, 5.11; N, 8.51. Found: C, 66.00; H, 5.15; N, 8.32.

EXAMPLE 18

1-Butyl-3-[2-[4-(4-fluorobenzoyl)piperidin-1-yl]ethyl]-thieno[2,3-d]pyrimidine-2,4-dione The title compound was prepared by the procedure of Example 14 using 2.0 g (5 mmol) of 3-[2-[4-(4-fluorobenzoyl)piperidin-1-yl]ethyl]thieno[2,3-d]pyrimidine-2,4-dione from Example 2 and bromobutane (819 mg, 6 mmol). There was obtained 774 mg (34% yield) of the title compound as a yellow solid after recrystallization from $CH_2Cl_2$/hexane, mp 124°–125° C.

Theor. $C_{24}H_{28}FN_3O_3S$: C, 63.00; H, 6.17; N, 9.18. Found: C, 63.11; H, 6.20; N, 9.35.

When in the above procedure, pentyl iodide, 1-bromo-2-methylpropane, 4-bromo-1-butene, 6-bromo-1-hexene or propargyl bromide is employed as the alkylating agent, the corresponding 1-pentyl, 1-(2-methylpropyl), 1-buten-4-yl), 1-(hexen-6-yl) or 1-(propyn-3-yl) derivative is obtained.

EXAMPLE 19

3-[4-[4-(4-Fluorobenzoyl)piperidin-1-yl]butyl]-thieno[3,4-d]pyrimidine-2,4-dione The title compound was prepared by the procedure of Example 10 using N-(4-bromobutyl)-N'-(4-carbomethoxythien-3-yl)urea (6.92 g, 21 mmol) and 4-(4-fluorobenzoyl)piperidine hydrochloride (10.16 g, 42 mmol). The urea was prepared by reacting methyl 4-aminothiophene-3-carboxylate with 4-bromobutylisocyanate in toluene at room temperature for 12 hours to produce the urea as a tan solid, mp 85°–86° C. There was obtained 3.62 g (40.8% yield) of the title compound as a brown solid. This material was recrystallized from $CH_2Cl_2$/ether, mp 190°–192° C.

Theor. $C_{22}H_{24}FN_3O_3S$: C, 61.52; H, 5.63; N, 9.78. Found: C, 61.58; H, 5.63; N, 9.73.

EXAMPLE 20

3-[5-[4-[Bis(4-fluorophenyl)methylene]piperidin-1-yl]pentyl]thieno[3,4-d]pyrimidine-2,4-dione The title compound was prepared by the procedure of Example 10 using N-(5-bromopentyl)-N'-(4-carbomethoxythien-3-yl)urea (9.01 g, 26 mmol) and 4-[bis(4-fluorophenyl)methylene]piperidine (14.76 g, 52 mmol). The urea was prepared by reacting methyl 4-aminothiophene-3-carboxylate with one equivalent of 5-bromopentylisocyanate in toluene at room temperature for four hours to produce the urea as a tan solid (98% yield). This material was recrystallized from $CH_2Cl_2$/ether/hexane to afford the urea as a white solid, mp 92°–93.5° C.

Theor. $C_{12}H_{17}BrN_2O_3S$: C, 41.26; H, 4.91; N, 8.02. Found: C, 41.52; H, 4.94; N, 7.98.

There was obtained 12.04 g (89% yield) of the title compound as a cream-colored solid after recrystallization from $CH_2Cl_2$/ether/hexane, mp 118°–122° C.

Theor. $C_{29}H_{29}F_2N_3O_2S$: C, 66.77; H, 5.60; N, 8.06. Found: C, 66.38; H, 5.44; N, 7.97.

EXAMPLE 21

3-[2-[4-[Bis(4-fluorophenyl)methylene]piperidin-1-yl]ethyl]-1-methylthieno[3,2-d]pyrimidine-2,4-dione, ¼ Hydrate A mixture of the 3-[2-[4-[bis(4-fluorophenyl)methylene]piperidin-1-yl]ethyl]thieno[3,2-d]pyrimidine-2,4-dione of Example 5 (2.0 g, 4.17 mmol) and sodium hydride (60% in oil, 0.182 g, 4.55 mmol) in dimethylformamide (40 ml) was equilibrated at room temperature for 1.5 hours. Methyl iodide (0.28 ml, 4.55 mmol) was added to the solution. The reaction mixture was stirred at room temperature for 16 hours. The solvent was evaporated in vacuo, and the residue was treated with water (50 ml). The resultant solid was collected by filtration, washed with water and air dried. The product was taken up in methylene chloride and eluted through a pad of magnesol using 2% methanol in methylene chloride as the eluant. The resultant colorless solid was recrystallized from ethanol to give the title compound (0.957 g, 46% yield) as a colorless solid, mp 146°–148° C. IR(KBr): 1500, 1650 and 1700 cm$^{-1}$; MS (DCI), m/z 494 (MH$^+$); $^1$H NMR (CDCl$_3$): δ 2.34 (t, J=5 Hz, 4H), 2.62 (t, J=5 Hz, 4H), 2.67 (t, J=7 Hz, 2H), 3.58 (s, 3H), 4.22 (t, J=7 Hz, 2H), 6.94–7.07 (m, 7H) and 7.72 (d, J=5 Hz, 1H).

For $C_{27}H_{25}F_2N_3O_2S·\frac{1}{4}H_2O$: Theor.: C, 65.10; H, 5.16; N, 8.43. Found: C, 65.13; H, 5.34; N, 8.33.

EXAMPLE 22

3-[2-[4-(4-Fluorobenzoyl)piperidin-1-yl]ethyl]-1-methylthieno[3,2-d]pyrimidine-2,4-dione A mixture of the 3-[2-[4-(4-fluorobenzoyl)piperidin-1-yl]ethyl]thieno[3,2-d]pyrimidine-2,4-dione of Example 1 (2.0 g, 4.98 mmol) and sodium hydride (60% in oil, 0.209 g, 5.23 mmol) in dimethylformamide (40 ml) was equilibrated at room temperature for one hour. Methyl iodide (0.34 ml, 5.48 mmol) was added to the solution. The reaction mixture was stirred at room temperature for 16 hours. The solvent was evaporated in vacuo and the residue was treated with water (50 ml). The resultant solid was collected by filtration, washed with water and air-dried. The product was taken up in methylene chloride and eluted through a pad of magnesol using 2% methanol in methylene chloride as the eluant to give the named compound (1.3 g, 63% yield) as a colorless solid, mp 171°–174° C. IR(KBr): 1490, 1650 and 1695 cm$^{-1}$; MS (DCI), m/z 416 (MH$^+$); $^1$H NMR (CDCl$_3$): δ 1.80–1.84 (m, 5H), 2.20–2.26 (m, 2H), 2.69 (t, J=7 Hz, 2H), 6.95 (d, J=5 Hz, 1H), 7.13 (t, J=9 Hz, 2H), 7.73 (d, J=5 Hz, 1H), 7.94–7.98 (m, 2H).

Theor. $C_{21}H_{22}FN_3O_3S$: C, 60.71; H, 5.34; N, 10.11. Found: C, 60.42; H, 5.28; N, 10.02.

When in the above procedure, pentyl iodide, 1-bromo-2-methylpropane, 4-bromo-1-butene, 6-bromo-1-hexene or propargyl bromide is employed as the alkylating agent, the corresponding 1-pentyl, 1-(2-methylpropyl), 1-buten-4-yl, 1-(hexen-6-yl) or 1-(propyn-3-yl) derivative is obtained.

EXAMPLE 23

3-[2-[4-[Bis(4-fluorophenyl)methylene]piperidin-1-yl]ethyl-1-methylthieno[3,4-d]pyrimidine-2,4-dione A mixture of the 3-[2-[4-[bis(4-fluorophenyl)methylene]piperidin-1-yl]ethyl]thieno[3,4-d]pyrimidine-2,4-dione of Example 4 (0.92 g, 1.92 mmol) and sodium hydride (60% in oil, 0.092 g, 2.3 mmol) in dimethylformamide (30 ml) was equilibrated at room temperature for one hour. Methyl iodide (0.16 ml, 2.53 mmol) was added to the solution. The reaction mixture was stirred at room temperature for 20 hours. The solvent was evaporated in vacuo, and the residue was treated with water (100 ml). The resultant solid was collected by filtration, washed with water and air dried. The product was purified by medium pressure chromatography on silica gel 60 using 2% methanol in methylene chloride as the eluant to give the title compound (0.150 g, 16% yield) as a colorless solid, mp 152°–153° C. IR(KBr): 1500, 1660 and 1705 cm$^{-1}$; MS (DCI), m/z 494 (MH$^+$); $^1$H NMR (CDCl$_3$): δ 2.33–2.36 (m, 4H), 2.61–2.66 (m, 6H), 3.50 (s, 3H), 4.18 (t, J=8 Hz, 2H), 6.58 (d, J=3 Hz, 1H), 6.93–7.25 (m, 8H) and 8.22 (d, J=3 Hz, 1H).

Theor. $C_{27}H_{25}F_2N_3O_2S$: C, 65.70; H, 5.11; N, 8.48. Found: C, 65.63; H, 5.15; N, 8.43.

EXAMPLE 24

3-[2-[4-Phenyl-1,2,3,6-tetrahydropyridin-1-yl]ethyl]-thieno[3,4-dy]pyrimidine-2,4-dione The title compound was prepared by the procedure of Example 10 using N-(2-chloroethyl)-N'-(4-carbomethoxythien-3-yl)urea (5.0 g, 19 mmol) and 4-phenyl-1,2,3,6-tetrahydropyridine hydrochloride (7.47 g, 38.2 mmol). There was obtained 3.41 g (50.6% yield) of the title compound as a tan solid after recrystallization from methanol/chloroform/ether, mp 209°–213° C. (dec).

Theor. $C_{19}H_{19}N_3O_2S$: C, 64.56; H, 5.42; N, 11.89. Found: C, 64.11; H, 5.33; N, 11.86.

EXAMPLE 25

Brain Serotonin (5-HT$_2$) Radioreceptor Assay

The test objects of this Example were rat frontal cortex membranes. Mebrane fragments were prepared from the frontal cortex dissected from brains obtained from female rats ($\approx$150 g). The 5-HT$_2$ sites were labeled with $^3$H-ketanserin. Membrane fragments, $^3$H-ketanserin and an unlabeled test compound were incubated for 15 minutes at 37° C. Compound bound to the receptor site was separated from the remaining unbound compound by vacuum filtration. The ability of a nonlabeled compound to compete with $^3$H-ketanserin for binding sites is a measure of the compound's affinity for the 5-HT$_2$ receptor. Specific binding was determined by the difference between total counts bound and counts bound in the presence of $10^{-6}$M methysergide.

Data is presented as the IC$_{50}$, the concentration of nonlabeled compound required to displace 50% of the $^3$H-ketanserin specifically bound to 5-HT$_2$ binding sites. The results of this test are presented in Table I below.

EXAMPLE 26

Brain Serotonin (5HT$_{1A}$) radioreceptor Assay

The text objects of this procedure were rat frontal cortex membranes. Membrane fragments were prepared from prefrontal cortex disected from brains obtained from female rats ($\approx$150 g). The 5HT$_{1A}$ sites were labeled with $^3$H-8-OH dipropylaminotetralin (8-OH-DPAT). Membrane fragments, $^3$H-8-OH DPAT, TRIS buffer (pH 7.4) and unlabeled compound were incubated for 10 minutes at 37° C. and then for 10 minutes at 4° C. Separation of bound from unbound $^3$H-8-OH DPAT was performed by vacuum filtration on a glass fiber disc. The ability of a compound to compete with $^3$H-8-OH DPAT for binding sites is a measure of the affinity of the compound for the 5HT$_{1A}$ receptor. Specific binding was determined by the difference between total counts bound and the counts bound in the presence of $1\times10^{-5}$ 5-hydroxytryptamine.

Data is presented as either the IC$_{50}$ (concentration required to displace 50% of the $^3$H-8-OH DPAT specifically bound to the 5HT$_{1A}$ binding sites) or the % displaced (% inhibition) at a given concentration of compound. Test results are presented in Table I below.

EXAMPLE 27

Inhibition of Serotonin-Induced Smooth Muscle Contractions

The test objects of this Example were canines and rabbits. Rabbits were sacrificed by T-61 injection and the thoracic aorta was removed immediately. The aorta was placed in warmed, oxygenated Krebs-Henseleit buffer. After the tissue was cleaned, a 2–3 mm wide strip was cut helically from each aorta. A strip of approximately 5 cm was suspended in Krebs-Henseleit buffer at 37° C. in a 25 ml tissue bath and the tissues equilibrated at an initial resting tension of 4 g for 90–120 minutes. An initial serotonin dose curve, 0.01–10 $\mu$M was then done on each tissue, followed by a 60 minute washout and reequilibration. The test drug was then added for a 10 minute preincubation and another serotonin dose curve was done using 0.01–100 $\mu$M.

Results are expressed as DR$_{10}$ values. This is the concentration of the compound required to shift the serotonin dose curve 10x to the right, i.e., the concentration of antagonist at which the concentration of serotonin required for 50% maximal contraction is increased ten-fold. Test results are presented in Table I below.

EXAMPLE 28

Platelet Aggegation Assay

Human blood was collected into tubes containing sodium citrate. The plasma was separated by centrifugation and was used as the source of platelets. Serotonin (5 $\mu$M) was used as the agonist to induce platelet aggregation. A control aggregation curve (as measured by the decrease in absorbance in transmitted light) was obtained in the presence of serotonin and in the absence of test compound. The test compound was added to an identical sample in a cuvette for one minute before addition of serotonin to yield the experimental curve. The IC$_{50}$ is the concentration of compound required to inhibit 50% of the aggregation induced by serotonin.

EXAMPLE 29

5HT$_2$ Blockade in vivo

Antagonism of 5HT induced pressor responses was used to assess 5HT$_2$ blockade in vivo. Spontaneously hypertensive rats were anesthetized with sodium pentobarbital (50 mg/kg, i.p.). The right carotid artery and vein were cannulated for pressure recording and drug injection, respectively. The trachea was cannulated, the rat placed on a respirator and ventilated with room air at 50–60 breaths/minute. Rats were pretreated with prazosin hydrochloride (1 mg/kg, i.v., blous) and pentolinium tartrate (5 mg/kg, i.v., bolus). After 10 minutes equilibration, the rat was challenged with 5HT (100 $\mu$g/kg) which elevates mean arterial pressure (MAP) 60–100 mmHg; non-responsive rats were discarded.

After a baseline had been reestablished, bolus injections of 5HT (100 $\mu$g/kg, i.v.) were given and the MAP responses were evaluated both pre- and post-drug administration. 5HT challenges were repeated 10 minutes after each dose of antagonist. Up to three cumulative doses of the antagonist were given to a single animal.

Potency of experimental drugs as antagonists of the 5HT-induced pressor response is calculated as an ED$_{50}$ (dose of experimental drug that attenuates 5HT-induced pressor responses by 50%). Test results are presented in Table I below.

EXAMPLE 30

Alpha$_1$ Blockade in vivo

The potency of these compounds as alpha$_1$ adrenergic antagonists was determined using the following procedure: adult male spontaneously hypertensive rats (SHR) were anesthetized and bilaterally vagotomized. A carotid artery and jugular vein were cannulated for monitoring mean arterial blood pressure and drug administration, respectively. The percent inhibition of alpha$_1$ adrenergic receptor activation was quantified by measuring pressor responses to phenylephrine before and after antagonist treatment. The dose of antagonist required to produce a 50% inhibition of the phenylephrine pressor response (ED$_{50}$) was calculated by regression analysis. Compounds were tested to the limits of their solubility for intravenous administration. Test results are presented in Table I below.

EXAMPLE 31

Antihypertensive Activity in Spontaneously Hypertensive Rats (SHR)

Antihypertensive activity was assessed using the following procedure. Adult male SHR were surgically prepared with arterial cannuli under light ether anesthesia and given 60–90 minute post-surgical recovery. Mean arterial pressure (MAP) was continuously monitored via the arterial line. After baseline MAP was recorded, groups of 3–6 SHR received a single dose of drug or vehicle (0.5% methylcellulose) administered by gavage at doses of 1 to 5 mg/kg.MAP was monitored for four hours post-dosing.

Maximal changes in MAP were reported. These results were statistically compared to the pre-drug baseline values using a Students t-test with significance at $p<0.05$. Test results are presented in Table I below.

EXAMPLE 32

Inhibition of 5-HTP-Induced Head Twitching

This test detects compounds with antagonistic activity of serotonin receptors in vivo, and is a modified procedure of Corne, Pickering and Warner, *Brit. J. Pharmacol.* 20, 106 (1963). Groups of male CD1 mice were fasted overnight but allowed water ad libitum. They were deprived of water during the course of the experiment. The mice were weighed and treated orally or parenterally with the test compound in a dose volume of 10 ml/kg. Doses of test substance were calculated based upon the active compound. Substances for oral administration were dissolved or suspended in a 0.5% aqueous methylcellulose (15 centipoises) vehicle containing 4 ml of Tween 80/l.

A dose of 160 mg/kg of L-5-hydroxytryptophan (5-HTP) was administered i.v. in a dose volume of 5 ml/kg after one hour. The test mouse was restrained in a rodent restrainer that allowed the tail to extend out the back. The tail was then placed in tepid (but not scalding) water for approximately 10 seconds to soften the skin and dilate the tail vein. A 1 ml syringe and 25 gauge (⅝ inch) needle was used to administer the 5-HTP solution into one of the lateral tail veins.

A timer was started after dosing with 5-HTP to the first animal of the test group. The mice were observed for the occurrence of the head twitch response during 10 minutes, commencing five minutes after the treatment of each mouse. A head twitch involves the head, neck and ears and has the appearance of an exaggerated pinal reflex. The number of head twitches for each individual vehicle-treated mouse were recorded to establish a historical baseline. Since compounds are routinely evaluated for complete blockade of head twitch, it is necessary to count only the number of treated mice that exhibit or fail to exhibit the 5-HTP-induced twitch response during the one-minute interval.

The active compounds in the test block the twitch response (the response rated all or none). Fisher's Exact Probability Test is used to compare the number of animals that exhibit or do not exhibit the head twitch in drug- and vehicle-treated groups. The doses of drugs that block the 5-HTP-induced twitch response in 50% of the animals ($ED_{50}$) were calculated by the method of probits. Test results are presented in Table I below.

TABLE I

Activity of Compounds of the Invention in Various Biological Test Systems

| Example | Example 25 Brain 5-HT$_2$ Receptor IC$_{50}$ (nM) | Example 26 Brain 5-HT$_1$ Receptor IC$_{50}$ (μM) | Example 27 5-HT-Induced Smooth Muscle Contraction DR$_{10}$ (nM) | Example 28 Platelet Aggregation IC$_{50}$ (μM) | Example 29 5-HT-Induced Pressor Response ED$_{50}$ (mg/kg) | Example 30 Phenylephrine-Induced Pressor Response ED$_{50}$ (mg/kg) | Example 31 Antihypertensive Activity, p.o. % AMAP @ (mg/kg) | Example 32 Inhibit. of 5-HTP-Head Twitch ED$_{50}$ (mg/kg, p.o.) |
|---|---|---|---|---|---|---|---|---|
| Ketanserin | 6.2 | 24.5 | 3.0 | 0.032 | 0.013 | 1.08 | −33% @ 5 | 0.67 |
| Ritanserin | 2.1 | 3.2 | 1.0 | 1.2 | 0.008 | 5.36 | — | 0.32 |
| 1 | 0.6 | 16 | 6.3 | 0.034 | 0.009 | >10 | −10% @ 5 | 2.1 |
| 2 | 1.6 | 24% @ 10 μM | — | — | 0.016 | <3.0 | — | 0.26 |
| 3 | 2.4 | 13% @ 1 μM | 22.9 | 8.0 | 0.025 | 10.0 | −4% @ 5 | Inact. @ 10 |
| 4 | 2.8 | 20% @ 1 μM | 16.5 | 5.3 | 0.16 | >10 | — | ≈10 |
| 5 | 7.0 | 3% @ 1 μM | 100.0 | 1.8 | 0.017 | >10 | — | 1.78 |
| 6 | 0.8 | 24% @ 1 μM | 8.99 | 4.5 | 0.23 | >3 | −13% @ 5 | — |
| 7 | 0.31 | 3% @ 1 μM | 20.0 | 2.5 | 0.038 | — | — | — |
| 8 | 200.0 | 0% @ 1 μM | 10.0 | — | 0.038 | — | — | Inact. @ 10 |
| 9 | 4.2 | 12% @ 1 μM | 10.0 | 6.25 | 0.02 | >10 | — | Inact. @ 10 |
| 10 | 0.33 | 12.0 | 5.24 | 0.02 | 0.888 | <10 | — | 0.63 |
| 11 | 12.5 | 0% @ 1 μM | — | 0.09 | 0.029 | 10.0 | — | — |
| 12 | 8.5 | 24% @ 1 μM | — | 0.10 | 44% @ 0.3 | — | — | 1.74 |
| 13 | 15.0 | 31% @ 1 μM | 30.0 | — | — | — | — | 1.98 |
| 14 | 7.0 | 31% @ 1 μM | — | 0.04 | 0.018 | <10 | — | 2.96 |
| 15 | 450.0 | 0% @ 1 μM | — | — | — | — | — | 1–10 |
| 16 | 7.0 | 2% @ 1 μM | 19.0 | 0.38 | 0.119 | — | — | — |
| 17 | 32.0 | 0% @ 1 μM | — | — | — | — | — | Inact. @ 10 |
| 18 | 23.0 | 17% @ 1 μM | — | — | — | — | — | Inact. @ 10 |
| 19 | 12.5 | 0.21 | — | — | — | — | — | 1–10 |
| 20 | 650.0 | 0.27 | 85.0 | 0.3 | — | — | — | — |
| 23 | 1.8 | 3.0 | 66.0 | 17.0 | >0.3 | — | — | — |
| 24 | 29.0 | 53% @ 1 μM | — | — | — | — | — | Inact. @ 10 |

What is claimed is:

1. A compound of the formula

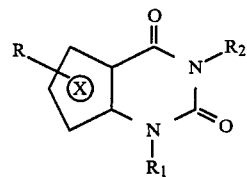

where 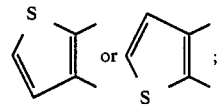 is O, S,

R is hydrogen, $C_1$–$C_3$ alkyl, Cl, Br or nitro;
$R_1$ is hydrogen, $C_1$–$C_6$ alkyl, $C_3$–$C_6$ branched-chain alkyl, $C_3$–$C_6$ alkenyl, $C_3$–$C_6$ alkynyl or —$COR_3$;
$R_2$ is

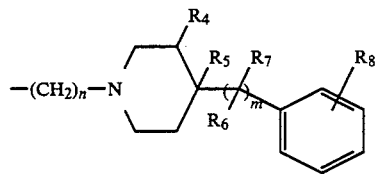

R₃ is C₁–C₆ alkyl, phenyl, nitro phenyl, acetamido phenyl or phenyl substituted with Cl, Br, F, I, C₁–C₃ alkyl, C₁–C₃ alkoxy, CF₃ or acetyl;
R₄ is hydrogen, or R₄ is a double bond, or R₅ together with R₆ is a double bond;
R₆ together with R₅ is a double bond or R₆ togther with R₇ is a carbonyl oxygen;
R₇ phenyl or phenyl substituted with Cl, Br, F, I, CF₃, C₁–C₃ alkyl or C₁–C₃ alkoxy, or R₇ together with R₆ is a carbonyl oxygen;
R₈ is hydrogen, Cl, Br, F, CF₃, C₁–C₆ alkyl or C₁–C₃ alkoxy;
m is 0 or 1; and
n is 2–6;
with the provisos that
when

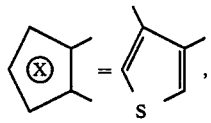

then R is not C₁–C₃ alkyl;
when

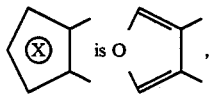

R is hydrogen,
when R₄ and R₅ are hydrogen, R₆ together with R₇ is a carbonyl oxygen and m is 1,
when R₄ is hydrogen and R₅ together with R₆ is a double bond, R₇ is phenyl or phenyl substituted with Cl, Br, F, I, CF₃, C₁–C₃ alkyl or C₁–C₃ alkoxy, and m is 1.

2. A compound of claim 1 wherein R₈ is F.
3. A compound of claim 2 wherein R₄ and R₅ are hydrogen.
4. A compound of claim 2 wherein R₄ is hydrogen and R₅ and R₆ are combined to form a double bond.
5. A compound of claim 4 wherein R₇ is phenyl substituted with F.
6. A compound of claim 2 wherein

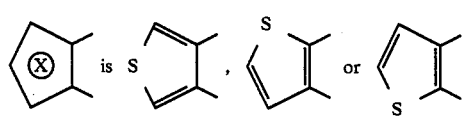

7. A compound of claim 3 wherein

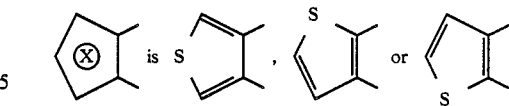

8. A compound of claim 4 wherein

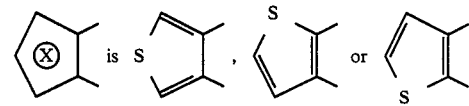

9. A compound of claim 5 wherein

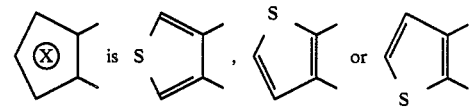

10. A compound of claim 4 wherein

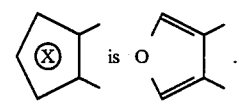

11. A compound of claim 5 wherein

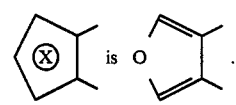

12. A compound of claim 1 selected from the group consisting of 3-[2-[4-(4-fluorobenzoyl)piperidin-1-yl]ethyl]thieno[3,2-d]pyrimidine-2,4-dione; 3-[2-[4-[bis (4-fluorophenyl)methylene]piperidin-1-yl]-ethyl]-thieno[3,2-d]pyrimidine-2,4-dione; 3-[2-[4-[bis(4-fluorophenyl)methylene]piperidin-1-yl]ethyl]-1-methyl-thieno[3,2-d]pyrimidine-2,4-dione; and 3-[2-[4-(4-fluorobenzoyl)piperidin-1-yl]ethyl]-1-methylthieno-[3,2-d]-pyrimidine-2,4-dione.

13. A compound of claim 1 selected from the group consisting of 3-[2-[4-(4-fluorobenzoyl)piperidin-1-yl]ethyl]thieno[2,3-d]pyrimidine-2,4-dione; 1-acetyl-3-[2-[4-(4-fluorobenzoyl)piperidin-1-yl]-ethyl]thieno[2,3-d]pyrimidine-2,4-dione; 3-[2-[4-[bis(4-fluorophenyl)methylene]piperidin-1-yl]-ethyl]thieno[2,3-d]pyrimidine-2,4-dione; and 1-butyl-3-[2-[4-(4-fluorobenzoyl)piperidin-1-yl]-ethyl]thieno[2,3-d]pyrimidine-2,4-dione.

14. A compound of claim 1 selected from the group consisting of 3-[2-[4-[bis(4-fluorophenyl)methylene]-piperidin-1-yl]ethyl]thieno[3,4-d]pyrimidine-2,4-dione; 3-[2-[4-[bis(4-fluorophenyl)methylene]-piperidin-1-yl]ethyl]-1-(2,2-dimethyl-1-oxopropylthieno[3,4-d]pyrimidine-2,4-dione; 1-benzoyl-3-[2-[4-[bis(4-fluorophenyl)methylene]piperidin-1-yl]-ethyl]thieno[3,4-d]pyrimidine-2,4-dione; 3-[2[4-(4-fluorobenzoyl)piperidin-1-yl]ethyl]thieno[3,4-d]-pyrimidine-2,4-dione; 1-acetyl-3-[2-[4-(4-fluorobenzoyl)piperidin-1-yl]ethyl]thieno[3,4-d]pyrimidine-2,4-dione; 1-benzoyl-3-[2-[4-(4 -fluorobenzoyl)piperidin-1-yl]ethyl]thieno[3,4 -d]pyrimidine-2,4-dione; 3-[2-[4-(4-fluorobenzoyl)piperidin-1-yl]ethyl]-1-(2,2-dimethyl-1-oxopropylthieno[3,4-d]pyrimidine-2,4- dione; 3-[2-[4-(4-fluorobenzoyl)piperidin-1-yl]ethyl]-1-methylthieno[3,4-d]pyrimidine-2,4-dione; 1-butyl-3-[2-[4-(4-fluorobenzoyl)piperidin-1-yl]ethyl]thieno[3,4-d]pyrimidine-2,4-dione; 3-[2-[4-(4-fluorobenzoyl)piperidin-1-yl]ethyl]-5-methylthieno-[3,4-d]pyrimidine-2,4-dione; 3-[2-[4-bis(4-fluorophenyl)methylene]piperidin-1-yl]ethyl]-5-methylthieno[3,4-d]pyrimidine-2,4-dione; 3-[4-[4-(4-fluorobenzoyl)piperidin-1-yl[butyl]-thieno[3,4-d]pyrimidine-2,4-dione; 3-[5-[4-[bis(4-fluorophenyl)methylene]piperidin-1-yl]pentyl]thieno[3,4-d]pyrimidine-2,4-dione; 3-[2-[4-[bis(4-fluorophenyl)methylene]piperidin-1-yl]ethyl]-1-methylthieno[3,4-d]pyrimidine-2,4-dione; and 3-[2-[4-phenyl-1,2,3,6-tetrahydropyridin-1-yl]ethyl]thieno[3,4-d]pyrimidine-2,4-dione.

15. A compound of claim 1 which is 3-[2-[4-[bis(4-fluorophenyl)methylene]piperidin-1-yl]ethyl]furo[3,4-d]pyrimidine-2,4-dione.

16. A compound of claim 1 which is 3-[2-[4-(4-fluorobenzoyl)piperidin-1-yl]ethyl]thieno[3,2-d]pyrimidine-2,4-dione.

17. A compound of claim 1 which is 1-acetyl-3-[2-[4-(4-fluorobenzoyl)piperidin-1-yl]ethyl]thieno[2,3-d]pyrimidine-2,4-dione.

18. A compound of claim 1 which is 3-[2-[4-[bis(4-fluorophenyl)methylene]piperidin-1-yl]ethyl]-thieno[2,3-d]pyrimidine-2,4-dione.

19. A pharmaceutical composition comprising as an active ingredient an effective amount of a compound of claim 1 and a suitable pharmaceutical carrier.

20. A pharmaceutical composition comprising as an active ingredient an effective amount of a compound of claim 12 and a suitable pharmaceutical carrier.

21. A pharmaceutical composition comprising as an active ingredient an effective amount of a compound of claim 13 and a suitable pharmaceutical carrier.

22. A pharmaceutical composition comprising as an active ingredient an effective amount of a compound of claim 14 and a suitable pharmaceutical carrier.

23. A pharmaceutical composition comprising as an active ingredient an effective amount of a compound of claim 15 and a suitable pharmaceutical carrier.

24. A method of treating hypertension in mammals by administering an effective amount of a compound of claim 1.

25. A method of treating hypertension in mammals by administering an effective amount of a compound of claim 12.

26. A method of treating hypertension in mammals by administering an effective amount of compound of claim 13.

27. A method of treating hypertension in mammals by administering an effective amount of a compound of claim 14.

28. A method of treating hypertension in mammals by administering an effective amount of a compound of claim 15.

29. A method of treating cardiovascular disease in mammals by administering an effective amount of a compound of claim 1.

30. A method of treating cardiovascular disease in mammals by administering an effective amount of a compound of claim 12.

31. A method of treating cardiovascular disease in mammals by administering an effective amount of a compound of claim 13.

32. A method of treating cardiovascular disease in mammals by administering an effective amount of a compound of claim 14.

33. A method of treating cardiovascular disease in mammals by administering an effective amount of a compound of claim 15.

34. A method of antagonizing the effects of serotonin in mammals by administering an effective amount of a compound of claim 1.

35. A method of antagonizing the effects of serotonin in mammals by administering an effective amount of a compound of claim 12.

36. A method of antagonizing the effects of serotonin in mammals by administering an effective amount of a compound of claim 13.

37. A method of antagonizing the effects of serotonin in mammals by administering an effective amount of a compound of claim 14.

38. A method of antagonizing the effects of serotonin in mammals by administering an effective amount of a compound of claim 15.

* * * * *